(12) United States Patent
Kataoka et al.

(10) Patent No.: US 8,592,385 B2
(45) Date of Patent: Nov. 26, 2013

(54) POLYMER MICELLE COMPLEX INCLUDING NUCLEIC ACID

(75) Inventors: Kazunori Kataoka, Tokyo (JP); Yuichi Yamasaki, Tokyo (JP); Seiji Takae, Tokyo (JP)

(73) Assignee: The University of Tokyo, Tokyo (JP)

( * ) Notice: Subject to any disclaimer, the term of this patent is extended or adjusted under 35 U.S.C. 154(b) by 544 days.

(21) Appl. No.: 12/281,124

(22) PCT Filed: Sep. 4, 2006

(86) PCT No.: PCT/JP2006/317920
§ 371 (c)(1),
(2), (4) Date: Sep. 22, 2008

(87) PCT Pub. No.: WO2007/099660
PCT Pub. Date: Sep. 7, 2007

(65) Prior Publication Data
US 2009/0258416 A1    Oct. 15, 2009

(30) Foreign Application Priority Data

Mar. 1, 2006   (JP) ................................. 2006-054332

(51) Int. Cl.
*C12N 15/85* (2006.01)
(52) U.S. Cl.
USPC ............................................ 514/44; 525/90
(58) Field of Classification Search
None
See application file for complete search history.

(56) References Cited

U.S. PATENT DOCUMENTS 7,780,957 B2 *   8/2010   Kataoka et al. ............ 424/78.17

FOREIGN PATENT DOCUMENTS

| EP | 1621569 | 2/2006 |
|----|---------|--------|
| WO | WO-96/32434 A1 | 10/1996 |
| WO | WO-96/33233 A1 | 10/1996 |
| WO | WO-97/06202 A1 | 2/1997 |
| WO | WO-2005/078084 | 8/2005 |

OTHER PUBLICATIONS

Takae et al. Polymer Preprints, Japan, vol. 54, No. 1, 2005, abstract.*
Seishi Takae et al., "Synthesis of Novel Poly (ethylene glycol)—Polycation Block Copolymer Possessing Disulfide Bond in the Main Chain: Application toward Non-Viral Gene Vector", Polymer Preprints, Japan, 2005, vol. 54, No. 1, p. 2203.
"Water-Soluble Polyion Complex Associates of DNA and Poly(ethylene glycol)-Poly(L-lysine) Block Copolymer" by Katayose et al., *Bioconjugate Chem.* 1997, 8, pp. 702-707.
"PEGylated Polyplex Micelles from Triblock Catiomers with Spatially Ordered Layering of Condensed pDNA and Buffering Units for Enhanced Intracellular Gene Delivery" by Fukushima et al., J. Am. Chem. Soc. 2005, 127, pp. 2810-2811.
"Water-soluble polyamides as potential drug carriers, II*", Amine-functionalized poly (α, β-D, L-aspartamide) derivatives**, Neuse et al., *Die Angewandte Makromolekulare Chemie* 181 (1990), pp. 153-170 (Nr. 3085).
"Water-soluble polyamides as potential drug carriers", III, Relative main-chain stabilities of side chain-functionalized aspartamide polymers on aqueous-phase dialysis*, Neuse et al., *Die Angewandte Makromolekulare Chemie* 192 (1991), pp. 35-50 (Nr. 3300).
English translation of Takae et al., Polymer Preprints, Japan, 2005;54(1): 193, Synthesis of Poly(ethylene glycol)-Polycation Block Copolymer Having Disulfide Bond in the Main Chain and its Application toward Gene Vector.
Takae et al., J. Am. Chem. Soc. 2008, 130, 6001-6009, PEG-Detachable Polyplex Micelles Based on Disulfide-Linked Block Catiomers as Bioresponsive Nonviral Gene Vectors.

* cited by examiner

*Primary Examiner* — Janet Epps-Smith
(74) *Attorney, Agent, or Firm* — McDermott Will & Emery LLP

(57) ABSTRACT

It is an object of the present invention to provide a polyion complex used as a non-viral gene vector, which achieves sufficiently high gene expression efficiency to a target cell. The polyion complex of the present invention comprises a block copolymer formed by binding polyethylene glycol to polycation via a disulfide group and a nucleic acid.

8 Claims, 11 Drawing Sheets

GPC charts of MeO-PEG-SS-NH₂

¹H NMR spectrum (in D₂O, Room temp)

¹H NMR spectrum (DMSO-d₆, 80 °C)

GPC chart of PEG-SS-P(Asp(DET))

$^1$H NMR spectrum (D$_2$O, 80 °C)

POLYMER MICELLE COMPLEX INCLUDING NUCLEIC ACID

CROSS-REFERENCE TO PRIOR APPLICATION

This is a U.S. National Phase Application under 35 U.S.C. §371 of International Patent Application No. PCT/JP2006/317920 filed Sep. 4, 2006, and claims the benefit of Japanese Patent Application No. 2006-054332, filed Mar. 1, 2006, both of which are incorporated by reference herein. The International Application was published in Japanese on Sep. 7, 2007 as WO 2007/099660 A1 under PCT Article 21(2).

TECHNICAL FIELD

The present invention relates to a polymer micelle complex containing a nucleic acid. More specifically, the present invention relates to the aforementioned complex used as a non-viral gene vector capable of responding to a reducing environment in a cell and delivering a nucleic acid into the cell.

BACKGROUND ART

Today, after completion of the decoding of the human genome, the correlation between genetic information and disease has been revealed. Under such circumstances, gene therapy for treating disease on a genetic level using a certain gene as a medicine is greatly expected as a method for treating various types of diseases, the treatment of which has been difficult so far.

In order to realize such gene therapy, it is essential to develop a vector that stably transfers a gene to a target site. The characteristics required for such a vector are: (1) a high stability in blood; (2) avoidance from uptake into reticuloendothelial system and renal clearance; (3) selective uptake into a target cell; (4) a smooth transfer into cytoplasm; and (5) low toxicity. That is to say, it is necessary for a gene vector to have two conflicting characteristics, namely, to stably encapsulate a gene therein until uptake into a target cell and to smoothly release the gene after the uptake into the cell (cytoplasm). A virus with excellent infectious ability satisfies such characteristics necessary for a gene vector, but a viral vector is accompanied with a problem regarding a risk of side effects. Thus, currently, attention has been focused on a non-viral gene vector.

As such a non-viral gene vector, a polyion complex (PIC) micelle, which is formed by electrostatic interaction between DNA acting as a polyanion and block copolymers composed of polyethylene glycol (PEG) and polycation (a cationic polypeptide), has been reported to date (please see S. Katayose et al., Bioconjugate Chem., 8, 702-707 (1997); S. Fukushima et al., J. Am. Chem. Soc., 127, 2810-2811 (2005)).

This PIC has a structure wherein the DNA is condensed as a result of the interaction of the DNA with the polycation portion in the block copolymer to form a core portion, and wherein the hydrophilic and bio-compatible PEG portion in the block copolymer forms a shell surrounding the core portion. Thus, the PIC is able to stably encapsulate DNA even in blood, for example. Moreover, since the PIC has a particle size of approximately 100 nm, which is almost the same level as that of virus, it is able to avoid the foreign substance-recognizing mechanism existing in vivo. Furthermore, since an ethylenediamine unit (—$CH_2$)$_2$—NH—($CH_2$)$_2$—$NH_2$) contained in the side chain of the polycation in the block copolymer has two pKa values, the PIC also has an advantage whereby endosomal escape is promoted by the proton sponge effect in a cell, while a complex with DNA is formed outside the cell. The aforementioned characteristics of the PIC enabled the improvement of gene expression efficiency.

DISCLOSURE OF THE INVENTION

It is an object of the present invention to provide a polyion complex exhibiting gene expression efficiency in a target cell, which is higher than that of the conventional polyion complex. It is another object of the present invention to provide a device and a kit for delivering a nucleic acid into a cell, using the aforementioned polyion complex.

The present inventor has conducted intensive studies directed towards achieving the aforementioned objects. As a result, the inventor has found that if a block copolymer formed by binding polyethylene glycol to a polycation via a disulfide bond (—S—S—) is used, the aforementioned goals can be achieved, thereby completing the present invention.

That is to say, the present invention includes the following features:

(1) A polyion complex, which comprises a block copolymer formed by binding polyethylene glycol to a polycation via a disulfide group, and a nucleic acid.

In the polyion complex of the present invention, an example of the polycation is a polypeptide having a cationic group at a side chain thereof. In addition, the block copolymer may be a polymer represented by the following general formula (1), for example:

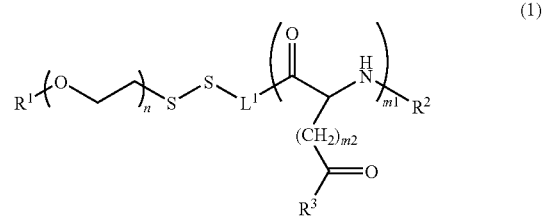

[wherein each of $R^1$ and $R^2$ independently represents a hydrogen atom or a substitutable linear or branched alkyl group containing 1 to 12 carbon atoms;

$R^3$ represents a residue derived from an amine compound having a primary amine;

$L^1$ represents NH, CO, a group represented by the following general formula (4):

$$-(CH_2)_{p1}-NH- \qquad (4)$$

(wherein p1 represents an integer between 1 and 5), or a group represented by the following general formula (5):

$$-L^{2a}-(CH_2)_{q1}-L^{3a}- \qquad (5)$$

(wherein $L^{2a}$ represents OCO, OCONH, NHCO, NHCOO, NHCONH, CONH or COO, $L^{3a}$ represents NH or CO, and q1 represents an integer between 1 and 5);

m1 represents an integer between 30 and 150; m2 represents an integer between 1 and 5; and n represents an integer between 100 and 400].

Herein, the —$R^3$ group in the polymer may be a group represented by the following general formula (2):

$$NH-(CH_2)_r-X^1 \qquad (2)$$

(wherein $X^1$ represents a primary, secondary or tertiary amine compound, or an amine compound residue derived from a quaternary ammonium salt, and r represents an integer between 0 and 5), or a group represented by the following general formula (3):

$$-[NH-(CH_2)_s]_t-X^2 \qquad (3)$$

(wherein $X^2$ represents a primary, secondary or tertiary amine compound, or an amine compound residue derived from a quaternary ammonium salt; and s and t are independent from each other and are also independent among the [NH—$(CH_2)_s$] units, and s represents an integer between 1 and 5 and t represents an integer between 2 and 5). More specifically, the $R^3$ may be —NH—$NH_2$ or —NH—$(CH_2)_2$—NH—$(CH_2)_2$—$NH_2$, for example.

Moreover, the polyion complex of the present invention may be a polyion complex wherein the polycation portion in the block copolymer and the nucleic acid bind to each other by electrostatic interaction. Furthermore, the polyion complex of the present invention may also be a polyion complex wherein the nucleic acid and the polycation portion in the block copolymer form a core portion, and wherein a portion containing polyethylene glycol in the block copolymer forms a shell portion around the core portion.

(2) A device for delivering a nucleic acid into a cell, which comprises the polyion complex according to (1) above.

(3) A kit for delivering a nucleic acid into a cell, which comprises a block copolymer formed by binding polyethylene glycol to polycation via a disulfide group.

In the kit of the present invention, an example of the aforementioned block copolymer is a polymer represented by general formula (1) (the same as described above).

(4) A block copolymer formed by binding polyethylene glycol to polycation via a disulfide group.

An example of the block copolymer of the present invention is a polymer represented by general formula (1) (the same as described above).

Further, in another aspect, the present invention provides a polyion complex, which comprises a block copolymer formed by binding polyethylene glycol to polycation via a disulfide group and an anionic substance. In this aspect, an example of the aforementioned block copolymer is a polymer represented by general formula (1) (the same as described above).

NUMERICAL EXPLANATION

Figure 1:
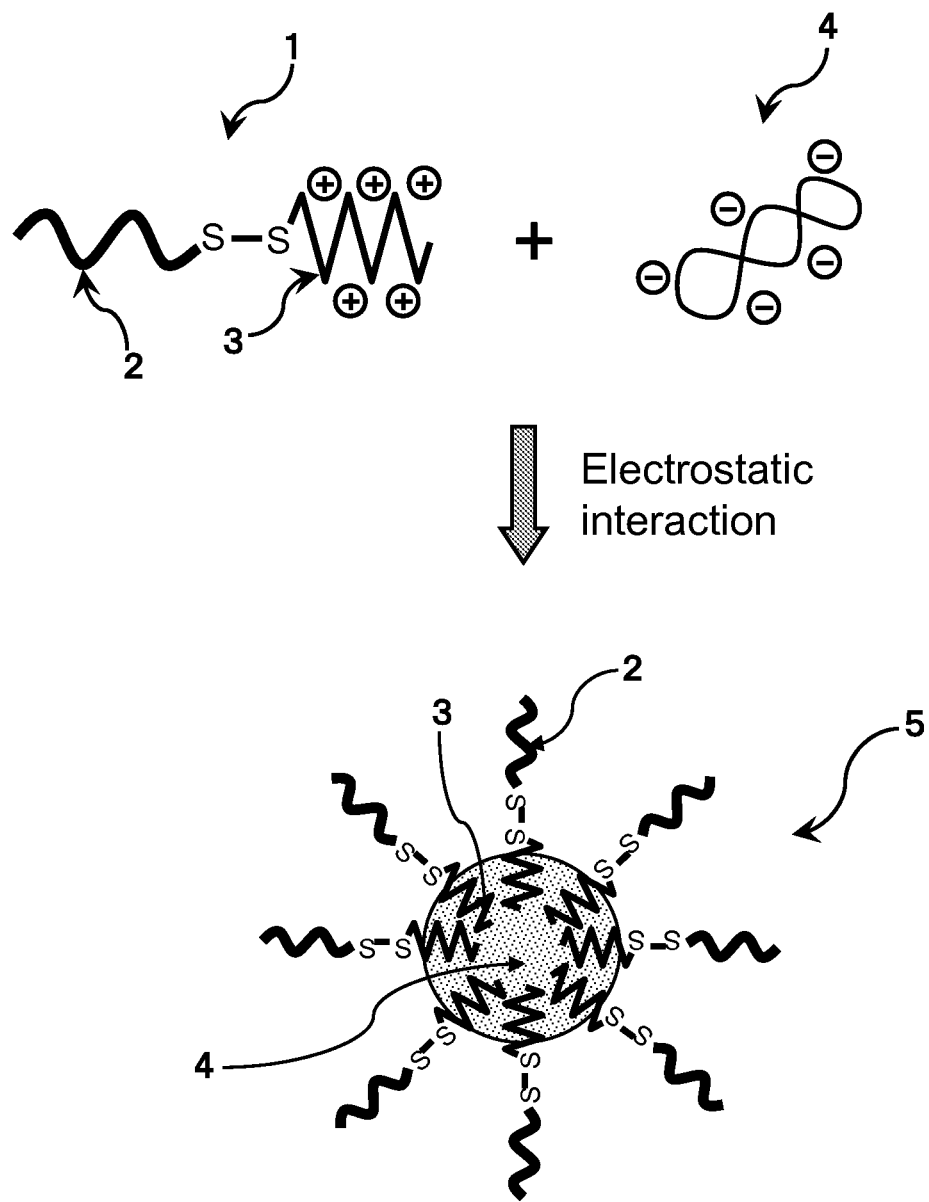
FIG. 1 is a schematic plane view showing the structure of the polyion complex of the present invention.

1. Block copolymer (PEG-SS-polycation)
2. Polyethylene glycol (PEG)
3. Polycation
4. Nucleic acid
5. Polyion complex (PIC)

BEST MODE FOR CARRYING OUT THE INVENTION

The present invention will be described in detail below. The examples that follow are provide to illustrate, but not limit, the claimed invention. It will be understood by those skilled in the art that various changes may be made without departing from the scope of the invention and the invention is not to be considered limited in scope to what is shown in the drawings and described in the specification.

The present specification includes all of the contents as disclosed in the specification and drawings of Japanese Patent Application No. 2006-054332, which is a priority document of the present application. In addition, all prior art publications, and publications of unexamined applications, patent publications and other patent documents cited herein are incorporated herein by reference in their entirety.

1. Summary of the Present Invention

In order to improve on the gene expression efficiency of the conventional polyion complex, the present inventor considered it necessary to separate a polyethylene glycol (PEG) portion of a block copolymer constituting a shell portion from the block copolymer in a target cell. This is based on the observation that, when compared with a polyion complex formed using a PEG-polycation (plus a nucleic acid), a polyion complex formed using polycation only (i.e., a polymer containing no PEG) and a nucleic acid exhibits extremely high gene expression efficiency when it is introduced into a cell in vitro.

Thus, the present inventor considered it optimal to use a polyion complex whose PEG portion is easily separated inside the target cell, in response to certain environmental changes occurring outside and/or inside a cell. The inventor focused on that fact that there is a difference in the oxidation-reduction environment between outside and inside of a cell due to a glutathione concentration difference (outside the cell (approximately 10 μM): oxidizing environment; inside the cell (approximately 10 mM): reducing environment). Based on the finding that a disulfide bond (—S—S—) is easily cleaved in the reducing environment, the inventor further studied a means for separating the PEG portion from the rest of the polyion complex in the reducing environment inside the cell.

As a result, the inventor synthesized a copolymer formed by binding PEG to polycation via a disulfide group as a block copolymer to be used. Thereafter, using the synthesized block copolymer and a nucleic acid, the inventor prepared a polyion complex micelle having a core-shell-type structure (please see FIG. 1).

Because of the effect of PEG in the polyion complex, the polyion complex maintains structural stability outside a cell, such as in blood After such a polyion complex has been incorporated into the cell, in response to a change to the reducing environment, the disulfide bond is cleaved, and the PEG portion is thereby easily separated. After separation of the PEG portion, substitution of the incorporated nucleic acid with polyanion existing in the cell is promoted, so that the polyion complex is dissociated. Thereby, the nucleic acid is smoothly released into the cytoplasm, resulting in a significant improvement of gene expression efficiency.

As stated above, a polyion complex composed of a block copolymer having a disulfide bond and a nucleic acid is extremely useful as an intelligent gene vector capable of efficient nucleic acid delivery into a cell, in response to an environmental change from outside to inside the cell.

2. Polyion Complex

The polyion complex (PIC) of the present invention is a nucleic acid-containing, micellar polymer complex, which is characterized in that it comprises a specific block copolymer having a disulfide bond and a nucleic acid.

(1) Block Copolymer

A specific block copolymer used as a constituent of the PIC of the present invention is a block copolymer comprising PEG and polycation as constituents, wherein these constituents bind to each other via a disulfide group.

The structures (e.g. degree of polymerization) of the aforementioned PEG and polycation are not limited, and any given structure can be selected. Among others, a polypeptide having a cationic group at the side chain thereof is preferable as a polycation. It is to be noted that the term "cationic group" used herein is not limited to a group that has already become cationic as a result of coordination of hydrogen ions, but it also includes a group that will become cationic if hydrogen ions are coordinated. Such a cationic group includes all known groups. Polypeptides having a cationic group at the side chain thereof include polypeptides formed by a peptide bond of known amino acids having a basic side chain (lysine, arginine, histidine, etc.) and polypeptides formed by subjecting various types of amino acids to a peptide bond and then substituting the side chain thereof such that it has a cationic group.

A specific example of the aforementioned specific block copolymer is preferably a block copolymer represented by the following general formula (1):

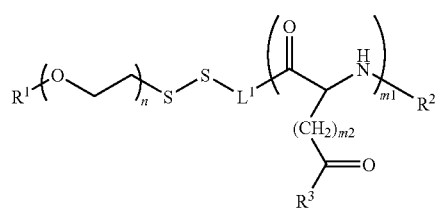

(1)

In the above general formula (1), each of $R^1$ and $R^2$ independently represents a hydrogen atom or a substitutable linear or branched alkyl group containing 1 to 12 carbon atoms.

Examples of the aforementioned linear or branched alkyl group containing 1 to 12 carbon atom include a methyl group, an ethyl group, an n-propyl group, an isopropyl group, an n-butyl group, a sec-butyl group, a tert-butyl group, an n-pentyl group, an n-hexyl group, a decyl group, and an undecyl group.

Examples of a substituent of the aforementioned alkyl group include an acetalized formyl group, a cyano group, a formyl group, a carboxyl group, an amino group, an alkoxycarbonyl group containing 1 to 6 carbon atoms, an acylamide group containing 2 to 7 carbon atoms, a siloxy group, a silylamino group, and a trialkylsiloxy group (each alkylsiloxy group independently contains 1 to 6 carbon atoms).

When the aforementioned substituent is an acetalized formyl group, it is hydrolyzed under acidic, moderate conditions, so as to convert it to another substituent, a formyl group (aldehyde group; —CHO). In addition, when the aforementioned substituent (in particular, a substituent in $R^1$) is a formyl group, a carboxyl group, or an amino group, antibodies, the fragments thereof, or other functional proteins or proteins with target directivity may be bind to the alkyl group via the aforementioned groups.

In the aforementioned general formula (1), $R^3$ that is a portion containing a cationic group represents a residue derived from an amine compound having a primary amine. An example of the —$R^3$ group is a group represented by the following general formula (2) or the following general formula (3), and among others, a group represented by the following formula (3) is preferable:

(2)

[wherein, in formula (2), $X^1$ represents a primary, secondary or tertiary amine compound, or an amine compound residue derived from a quaternary ammonium salt; and r represents an integer between 0 and 5]; or

(3)

[wherein, in formula (3), $X^2$ represents a primary, secondary or tertiary amine compound, or an amine compound residue derived from a quaternary ammonium salt; and s and t are independent from each other and are also independent among the [NH—$(CH_2)_s$] units, and s represents an integer between 1 and 5 (preferably 2) and t represents an integer between 2 and 5 (preferably 2)].

In general formulae (2) and (3), preferred examples of the —$X^1$ and —$X^2$ groups (amine compound residues) at the termini include —$NH_2$, —NH—$CH_3$, —N$(CH_3)_2$, groups represented by the following formulae (i) to (viii), and the like. Of these, —$NH_2$ is particularly preferable. In the following formula (vi), Y is a hydrogen atom, an alkyl group (containing 1 to 6 carbon atoms), or an aminoalkyl group (containing 1 to 6 carbon atoms), for example.

(i)

(ii)

(iii)

(iv)

(v)

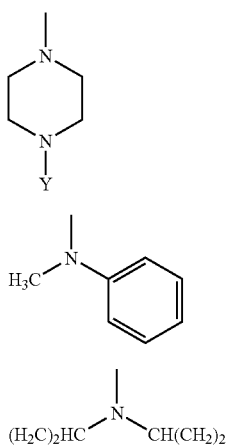

In general formula (1), specifically, the —$R^3$ group is particularly preferably "—NH—$NH_2$" or "—NH—$(CH_2)_2$—NH—$(CH_2)_2$—$NH_2$." The latter containing an ethylenediamine unit is more preferable. The aforementioned "—NH—$(CH_2)_2$—NH—$(CH_2)_2$—$NH_2$" indicates two steps involving pKa of 6.0 and 9.5. When the aforementioned substance forms a complex at pH 7.4, it is in a gauche-type single protonated state (see the following Reaction Formula 1). Thus, it is able to electrostatically interact with a nucleic acid. On the other hand, in the endosome (pH 5.5), the aforementioned "—NH—$(CH_2)_2$—NH—$(CH_2)_2$—$NH_2$" is further protonated, and it is converted to an anti-type (please refer to the following Reaction Formula 1). Thus, it has an effect of promoting endosomal escape due to the buffer effect.

A block portion having a side chain electrostatically bound to a nucleic acid (a block portion with a polymerization degree of m1 having a cationic group at the side chain thereof: polycation portion)

A block portion consisting of a polyethylene glycol (PEG) chain that is hydrophilic and excellent in terms of bio-compatibility (a block portion with a polymerization degree of n: PEG portion)

The molecular weight (Mw) of the block copolymer represented by general formula (1) is not limited, but it is preferably between 23,000 and 45,000, and more preferably between 28,000 and 34,000. In addition, with regard to individual block portions, the molecular weight (Mw) of the PEG portion is preferably between 8,000 and 15,000, and more preferably between 10,000 and 12,000, whereas the molecular weight (Mw) of the polycation portion is preferably between 15,000 and 30,000, and more preferably between 18,000 and 22,000.

A method for producing the polymer represented by general formula (1) is not limited. Examples of such a production method include: a method comprising previously synthesizing a segment (a PEG segment) containing —$R^1$ and a block portion of PEG chain, polymerizing predetermined monomers to one terminus of the PEG segment (the terminus opposite to the —$R^1$) in a predetermined order, and then substituting or converting the side chain thereof such that it comprises a cationic group, as necessary; and a method comprising previously synthesizing the aforementioned PEG segment and a block portion having a side chain containing a cationic group and then ligating these components to each other. Various methods and conditions for various types of reactions used in the production methods can be selected or determined in accordance with ordinary methods.

The aforementioned PEG segment can be prepared by the method for producing a PEG segment portion of a block Reaction formula 1

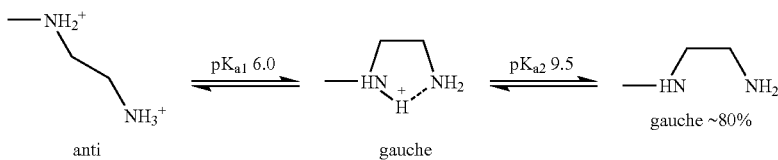

In general formula (1), $L^1$, which acts as a linker portion together with a disulfide bond (—S—S—), represents NH, CO, a group represented by the following general formula (4):

—$(CH_2)_{p1}$—NH—  (4)

[wherein p1 represents an integer between 1 and 5 (preferably 2 or 3)], or a group represented by the following general formula (5):

-$L^{2a}$-$(CH_2)_{q1}$-$L^{3a}$-  (5)

[wherein $L^{2a}$ represents OCO, OCONH, NHCO, NHCOO, NHCONH, CONH or COO, $L^{3a}$ represents NH or CO, and q1 represents an integer between 1 and 5 (preferably 2 or 3)].

In general formula (1), each of m1 and n represent the number of repeating units (polymerization degree) of each block portion. Specifically, m1 represents an integer between 30 and 150 (preferably 60 to 100); n represents an integer between 100 and 400 (preferably 200 to 300); and m2 represents an integer between 1 and 5 (preferably 1 or 2)].

As stated above, it can be said that the polymer represented by general formula (1) is a polymer having the following two block portions as essential constituents.

copolymer described in WO96/32434, WO96/33233, and WO97/06202, for example. The terminus opposite to the —$R^1$ group of the PEG segment is a portion corresponding to "S—S-$L^1$" in general formula (1). Preferred examples of such a terminus opposite to the —$R^1$ group include —S—S—$NH_2$, —S—S—COOH, a group represented by the following general formula (6):

—S—S—$(CH_2)_{p2}$—$NH_2$  (6)

[wherein p2 represents an integer between 1 and 5 (preferably 2 or 3)], and a group represented by general formula (7):

—S—S-$L^{2b}$-$(CH_2)_{q2}$-$L^{3b}$  (7)

[wherein $L^{2b}$ represents OCO, OCONH, NHCO, NHCOO, NHCONH, CONH, or COO; $L^{3b}$ represents $NH_2$ or COOH; and q2 represents an integer between 1 and 5 (preferably 2 or 3)].

An example of a specific method for producing the polymer represented by general formula (1) is a method, which comprises: polymerizing N-carboxylic anhydride (NCA) of protected amino acid, such as β-benzyl-L-aspartate (BLA) and Nε-Z-L-lysine, to the amino acid terminus of a PEG segment derivative having an amino acid group at the terminus thereof via a disulfide group, so as to synthesize a block copolymer; and then substituting or converting the side chain of each block portion with diethylene triamine (DET) or the like, such that the side chain of each block portion has the aforementioned cationic group.

(2) Nucleic Acid

In the PIC of the present invention, the type of a nucleic acid acting as a constituent of a core portion is not limited. Examples of such a nucleic acid include various types of DNA, RNA, and PNA (peptide nucleic acid), which can be used in gene therapy or the like. Preferred examples include plasmid DNA, antisense oligo DNA, and siRNA.

Since nucleic acid molecules become a polyanion, they are able to bind to the side chain of the polycation portion of the aforementioned block copolymer by electrostatic interaction.

In the present invention, the core portion may comprise various substances whose functions are expressed in a cell, such as a physiologically active protein and various types of peptides, in addition to the aforementioned nucleic acid, as necessary.

Moreover, in another aspect of the PIC of the present invention, a high-molecular-weight or low-molecular-weight "anionic substance" can be used as a constituent of the core portion. Examples of such an anionic substance include: high-molecular-weight substances such as a peptide hormone, a protein, an enzyme and a nucleic acid (DNA, RNA, or PNA); and low-molecular-weight substances (water-soluble compounds) having a charged functional group in a molecule thereof. In addition, this anionic substance includes a substance capable of changing the charged state of molecules having multiple functional groups in different charged states (anionic groups and cationic groups) to an anionic state by changing pH. Such anionic substances may be used singly or in combination of two or more types. It is not limited.

(3) Polyion Complex (PIC)

The PIC of the present invention may be a core-shell-type micelle complex, wherein a nucleic acid interacts with a portion (a polycation portion) of the aforementioned block copolymer to form a core portion, and wherein another portion of the aforementioned block copolymer (a portion containing a PEG portion) forms a shell portion around the aforementioned core portion (please see FIG. 1).

The PIC of the present invention can be easily prepared by mixing a nucleic acid with a block copolymer in any given buffer (e.g. Tris buffer, etc.), for example.

The mixing ratio between a block copolymer and a nucleic acid is not limited. For example, the ratio (N/P ratio) between the total number (N) of cationic groups (e.g. amino groups) in such a block copolymer and the total number (P) of phosphate groups in such a nucleic acid is preferably 1.5 to 60, more preferably 1.5 to 32, and further more preferably 2 to 8. In particular, when the block copolymer is the copolymer represented by the aforementioned general formula (1), the N/P ratio is not limited. However, it is preferably 1.5 to 32, more preferably 1.5 to 8, further more preferably 2 to 8, and particularly preferably 4 to 6 (in this case, N indicates the total number of primary amines and secondary amines contained in the side chain of the polycation portion). When the N/P ratio is within the aforementioned range, it is preferable in that free polymers do not exist and in that high expression efficiency is obtained in vivo. The aforementioned cationic group (N) means a group capable of electrostatically interacting with a phosphate group in the incorporated nucleic acid, so as to form an ionic bond.

The size of the PIC of the present invention is not limited. For example, a particle size is preferably between 30 and 150 nm, and more preferably between 50 and 100 nm, according to the dynamic light scattering.

3. Nucleic Acid-Delivering Device

The present invention provides a device for delivering a nucleic acid into a cell, which comprises the aforementioned polyion complex (PIC). The nucleic acid-delivering device of the present invention can be used as a means for efficiently introducing a desired nucleic acid contained in the core portion of PIC into a target cell, utilizing a change in the oxidation-reduction environment between inside and outside of a cell.

Specifically, a solution that contains PIC including a desired nucleic acid is administered to a test animal, so that the PIC can be introduced into the target cell in the body. Thereafter, when the PIC introduced into the cell is transferred from the endosome to the cytoplasm, the disulfide bond in the block copolymer is cleaved in response to the reducing environment in the cytoplasm, so that the PEG portion is separated. As a result, substitution of the nucleic acid contained in the PIC with polyanion existing in the cell is promoted, and thus the PIC is dissociated, so as to release the desired nucleic acid into the cytoplasm.

The nucleic acid-delivering device of the present invention can be applied to various types of animals such as a human, a mouse, a rat, a rabbit, a swine, a dog, and a cat, and thus the target animals are not limited. As an administration method to test animals, parenteral administration such as intravenous drip infusion is generally adopted. Various conditions such as a dose, the number of doses and an administration period can be determined, as appropriate, depending on the type of a test animal and the condition thereof.

The nucleic acid-delivering device of the present invention can be used in a therapy for introducing a desired nucleic acid into a cell that causes various types of diseases (gene therapy). Accordingly, the present invention can also provide a pharmaceutical composition comprising the aforementioned PIC, and a method for treating various types of diseases using the aforementioned PIC (in particular, gene therapy). It is to be noted that methods and conditions applied for administration are the same as those described above.

The aforementioned pharmaceutical composition can be prepared according to a common method by selecting and using, as appropriate, agents that are commonly used in drug manufacturing, such as an excipient, a filler, an extender, a binder, a wetting agent, a disintegrator, a lubricant, a surfactant, a dispersant, a buffer, a preservative, a solubilizer, an antiseptic, correctives, a soothing agent, a stabilizer, and an isotonizing agent. As the form of such a pharmaceutical composition, intravenous injection (including drops) is generally adopted. For example, the pharmaceutical composition of the present invention is provided in the form of a single dose ampule or a multidose container.

The aforementioned pharmaceutical composition and therapeutic method are effectively applied to cancer, for example.

4. Nucleic Acid-Delivering Kit

The nucleic acid-delivering kit of the present invention is characterized in that it comprises the aforementioned specific block copolymer. This kit can be preferably used in gene therapy for various types of target cells such as cancer cells, etc.

In the kit of the present invention, the preservation state of the block copolymer is not particularly limited. Taking into consideration their stability (preservative quality), usability, etc., the block copolymer can be preserved in the form of a solution, powders, etc.

The kit of the present invention may comprise other constituents, as well as the aforementioned specific block copolymer. Examples of such other constituents include various types of buffers, various types of nucleic acids (plasmid DNA, antisense oligo DNA, siRNA, etc.) to be introduced into cells, a buffer used for dissolution, various types of proteins, and instruction for use (manual for use).

The kit of the present invention is used to prepare a polyion complex (PIC) comprising, as a core portion, a desired nucleic acid to be introduced into a target cell. The prepared PIC can be effectively used as a device for delivering a nucleic acid into a target cell.

The present invention will be more specifically described in the following examples. However, these examples are not intended to limit the scope of the present invention.

EXAMPLE 1

Preparation of Polyion Complex (PIC)

(1) Synthesis of Block Copolymer

The reaction as shown in the following scheme 1 was carried out to obtain a block copolymer (PEG-SS-P(Asp(DET)) wherein polyethylene glycol binds to polycation via a disulfide bond. Individual reaction steps as shown in scheme 1, namely, the synthesis of PEG-SS-NH$_2$, the synthesis of PEG-SS-PBLA, and the synthesis of PEG-SS-P(Asp(DET)) will be described below.

(1-1) Synthesis of PEG-SS-NH$_2$

PEG-SH (Mn=10,227), a PEG segment formed by introducing a thiol group into one terminus of PEG (polymerization degree (n)=227), was purchased from NOF Corporation.

1 g of the PEG-SH and 0.77 g of 2-aminoethanethiol (in an amount of 100 times greater) were dissolved in 100 mL of MeOH, and the mixture was then reacted by stirring at room temperature for 13 days (GPC measurement conducted 4, 6, 8, and 13 days after initiation of the stirring). The obtained reaction product was dialyzed to MeOH, and it was then purified by ion exchange chromatography, so as to obtain PEG-SS—NH$_2$. A portion of the reaction product was sampled 4, 6, 8 and 13 days after initiation of the stirring, after completion of the dialysis, and after completion of the ion exchange chromatography, and it was then subjected to GPC measurement.

Figure 2:
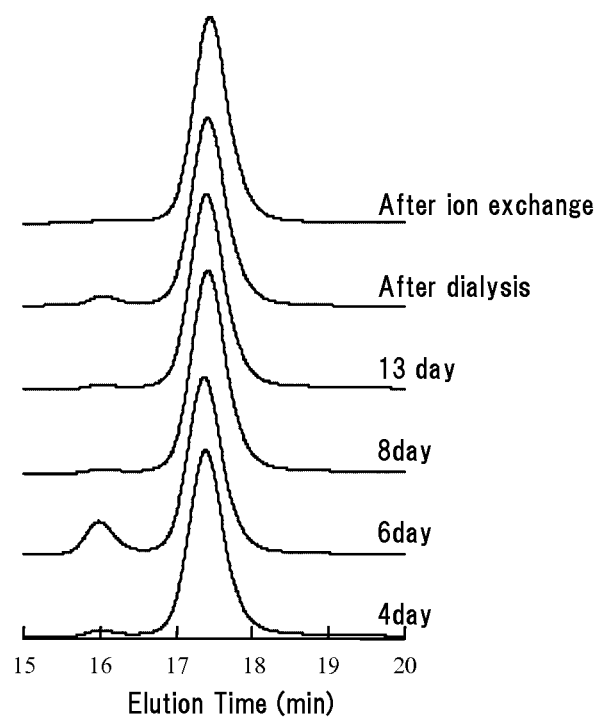
FIG. 2 is a view showing Gel Permeation Chromatography (GPC) charts of the synthetic process of PEG-SS-$NH_2$ over time.

FIG. 2 shows a summary of GPC charts. Looking at the results over time, dimers of PEG once increased, and they then decreased. Thus, it is considered that PEG segments bound to one another via an S—S bond to form dimers at the initiation stage of reaction, and that it was then gradually

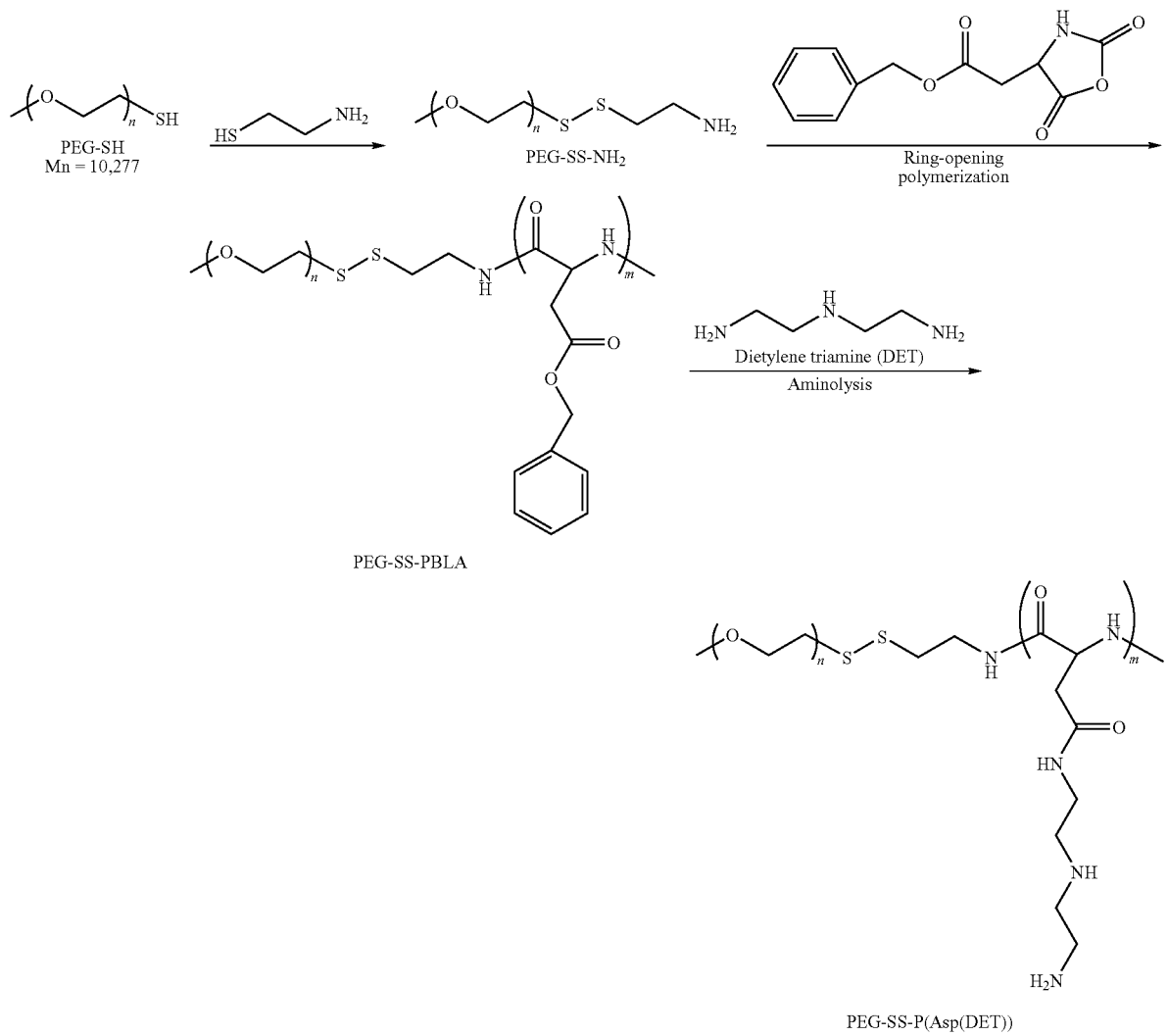

Scheme 1 replaced with 2-aminoethanthiol. Eight days after initiation of the stirring, almost no such dimers were observed. Thus, it is considered that the reaction was substantially completed for 8 days. In addition, there had been a fear that the exchange of the S—S bond might occur due to methanol dialysis and ion exchange after completion of the reaction. However, from the GPC results, it was confirmed that such S—S bond exchange hardly occurred.

The yield of PEG-SS-$NH_2$ was found to be 57% (0.57 g).

Figure 3:
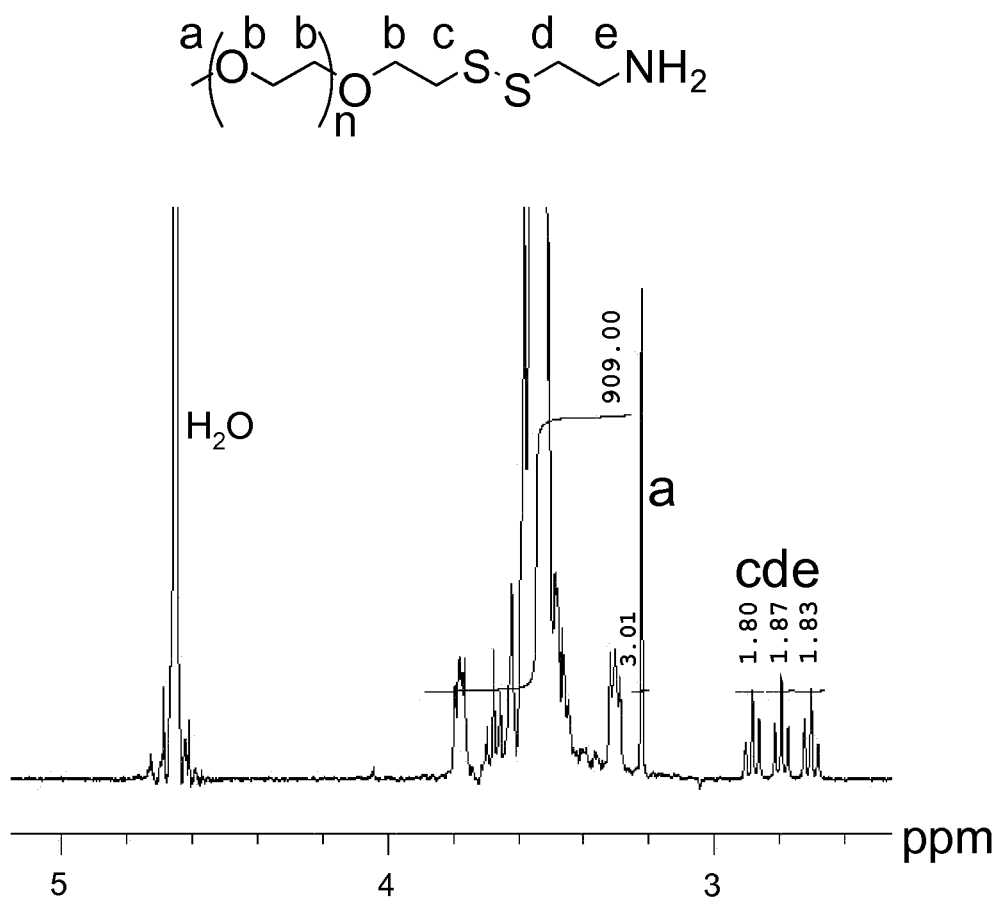
FIG. 3 is a view showing a $^1$H NMR spectrum of PEG-SS-$NH_2$.

Based on the $^1H$ NMR spectrum as shown in FIG. 3, the introduction rate of aminoethanthiol was found to be 93%. Thus, quantitative introduction was confirmed.

(1-2) Synthesis of PEG-SS-PBLA 300 mg of PEG-SS-$NH_2$ was dissolved in 4.5 mL of $CH_2Cl_2$, and 859 mg of β-benzyl-L-aspartate-N-carboxyanhydride (BLA-NCA) dissolved in 11.5 mL of $CH_2Cl_2$/DMF (10:1) was then added to the solution. The obtained mixture was stirred at 35° C. for 2 days. It was confirmed by IR that a peak derived from BLA-NCA had disappeared, and thus that the reaction had been completed. Thereafter, the reaction product was reprecipitated in 200 mL of hexane/ethyl acetate (6:4), followed by suction filtration. The resultant was then purified by drying under reduced pressure, so as to obtain "PEG-SS-PBLA."

Figure 4:
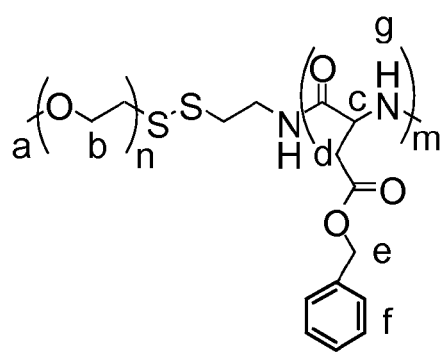
FIG. 4 is a view showing a $^1$H NMR spectrum of PEG-SS-PBLA.
Figure 4:
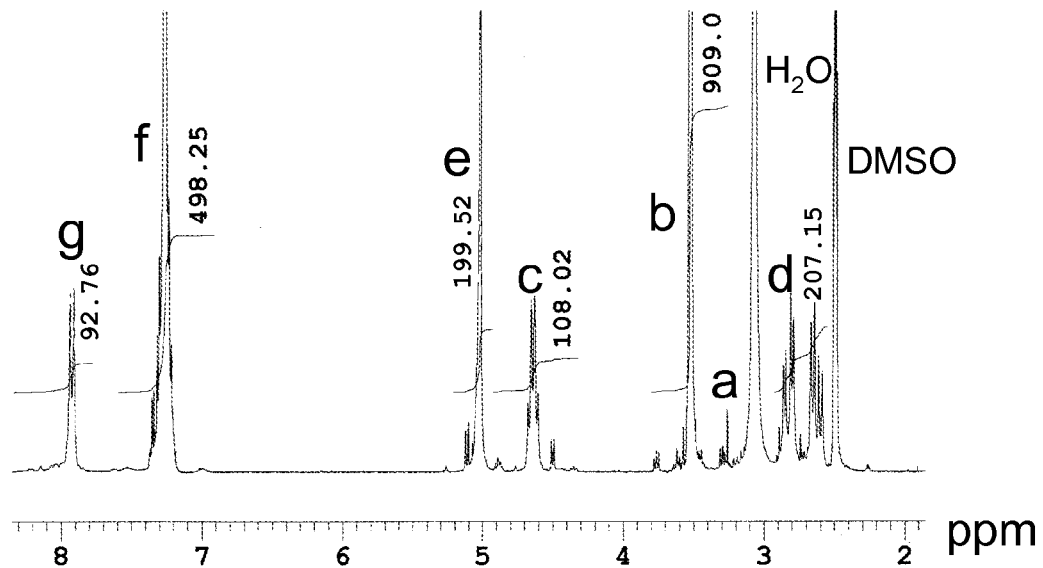

A peak derived from poly BLA (PBLA) was observed on the $^1H$-NMR spectrum as shown in FIG. 4. Thus, it was confirmed that polymerization of BLA-NCA had progressed. Using peak b of the main chain of PEG as a standard, by comparing the integration value of peak f of the benzene ring at the side chain of the PBLA portion therewith, the polymerization degree (m) of the PBLA portion was calculated to be 100. The yield of PEG-SS-PBLA was found to be 910 mg.

(1-3) Synthesis of PEG-SS-P(Asp(DET))

Diethylene triamine (DET) was introduced into the side chain of the PBLA portion of the obtained PEG-SS-PBLA (aminolysis reaction), so as to obtain polycation. Since an S—S bond is weak in alkali and an excessive amount of amine exists in the aminolysis reaction, it is necessary to introduce DET into the aforementioned side chain, while paying attention on prevention of the exchange of such S—S bond.

Specifically, 2 mL of N,N-dimethylformamide (DMF) was added to 40 mg of PEG-SS-PBLA, and the mixture was then stirred. Thereafter, 0.73 mL of DET in an amount of 50 times greater was added to the reaction product, and the obtained mixture was further stirred at room temperature for 3 minutes. After completion of the stirring, the reaction mixture was added dropwise to 15 mL of 5% AcOHaq. Finally, the resultant was dialyzed to 0.01 N HCl, followed by freeze-drying, so as to recover the reaction product.

Figure 5:
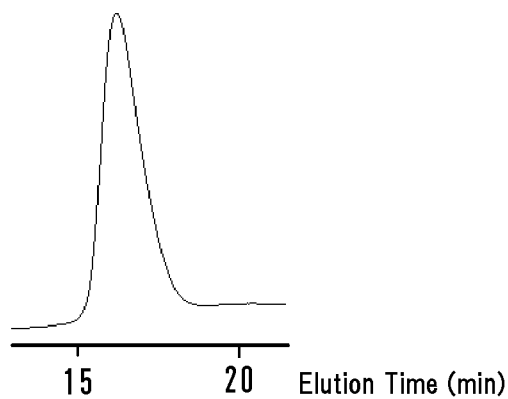
FIG. 5 is a view showing a GPC chart of PEG-SS-P(Asp(DET)).

A unimodal peak was confirmed on the GPC chart as shown in FIG. 5. Thus, it is considered that the cleavage or exchange of the S—S bond did not occur.

Figure 6:
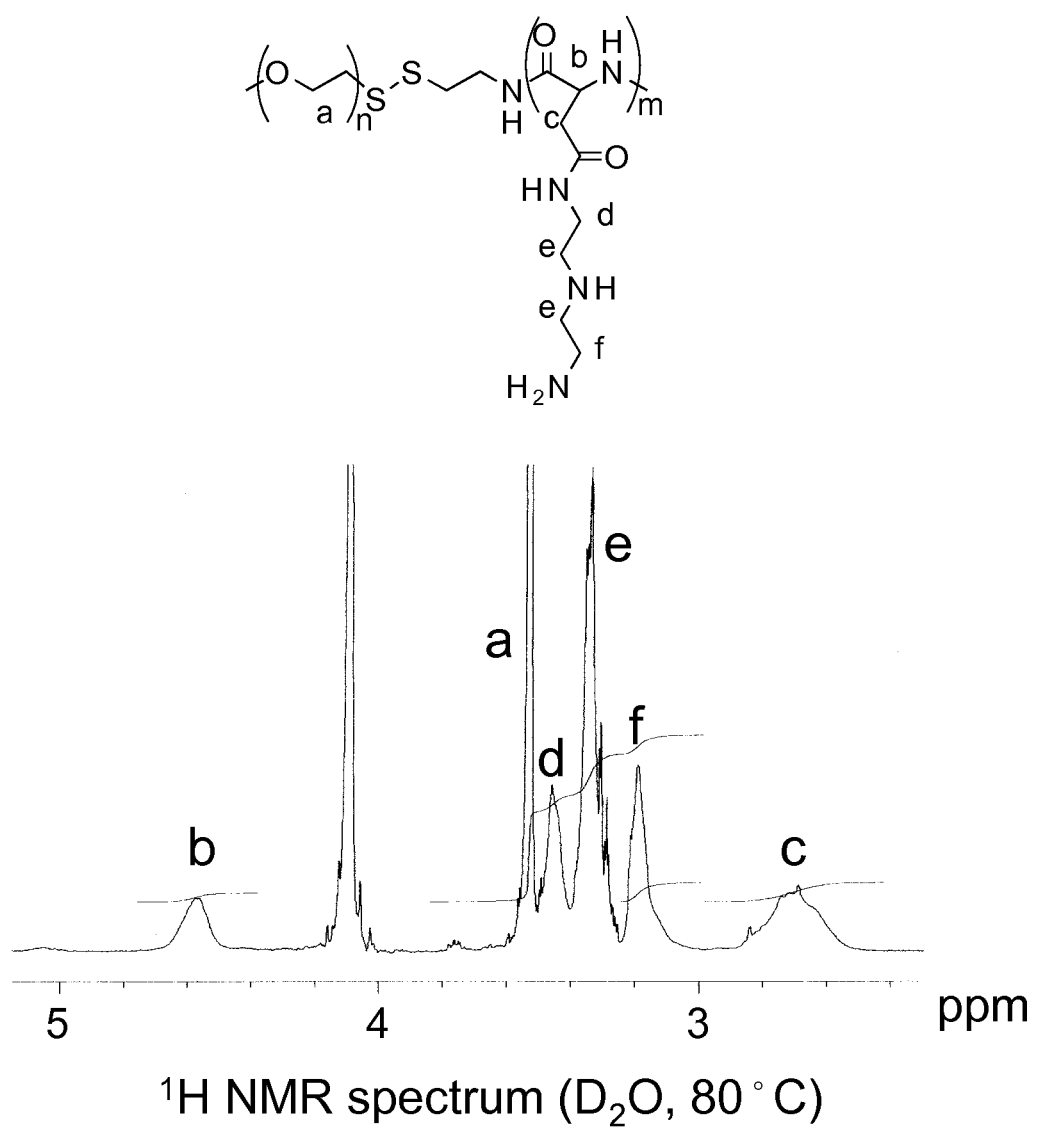
FIG. 6 is a view showing a $^1$H NMR spectrum of PEG-SS-P(Asp(DET)).

A DET-derived peak was observed on the $^1H$ NMR spectrum as shown in FIG. 6, and further, quantitative introduction of DET was also confirmed based on the integration ratio between peak c used as a standard and peak f.

In this way, PEG-SS-P(Asp(DET)), a block copolymer of interest, wherein PEG bound to polycation (an amino acid polymer formed by binding an ethylenediamine unit to an asparagine skeleton) via an S—S— bond, was obtained. As described above, the polymerization degree (n) of the PEG portion was found to be 227, and the polymerization degree (m) of the polycation portion was found to be 100.

(2) Used Nucleic Acid

As a nucleic acid to be delivered into a cell, a luciferase expression plasmid acting as a reporter gene (manufactured by Promega; production name: pGL3; hereinafter referred to as "pDNA") was used.

(3) Preparation of PIC pDNA was mixed with PEG-SS-P(Asp(DET)) in a 10 mM Tris buffer (pH 7.4) to prepare PIC containing the pDNA as a core portion. Specifically, PEG-SS-P(Asp(DET)) dissolved in 50 μL of a 10 mM Tris buffer was added to the pDNA (concentration: 50 μg/mL) dissolved in 100 μL of the same above buffer, so as to obtain a solution containing PIC.

It is to be noted that, as such PIC, the amount of PEG-SS-P(Asp(DET)) dissolved was adjusted, as appropriate, and those having the N/P ratios (please refer to the following formula) of 0, 1, 1.5, 2, 2.5, 3, 4, 8, 16 and 32 were individually prepared.

N/P ratio=[the total number of amino groups at the side chain of a polycation portion (the sum of primary amines and secondary amines)]/[the total number of phosphate groups of pDNA]

(4) Confirmation of PIC Formation

Agarose gel electrophoresis and ethidium bromide assay were performed to evaluate formation of PIC in the solution obtained in (3) above.

Figure 7:
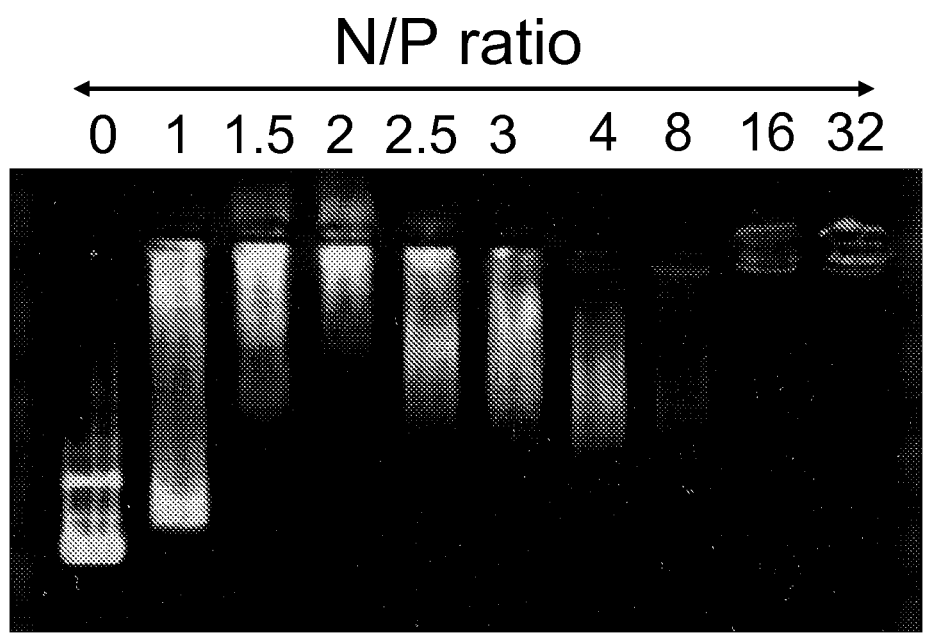
FIG. 7 is a photograph showing the results of the agarose gel electrophoresis of PIC using PEG-SS-P(Asp(DET)).

A loading buffer was added to the solution obtained in (3) above, and agarose gel electrophoresis was then performed. The results are shown in FIG. 7. A free pDNA band existed in case of N/P=1 or less, and such a free pDNA band disappeared in case of N/P=1.5 or more. From these results, it is considered that PIC was formed.

Figure 8:
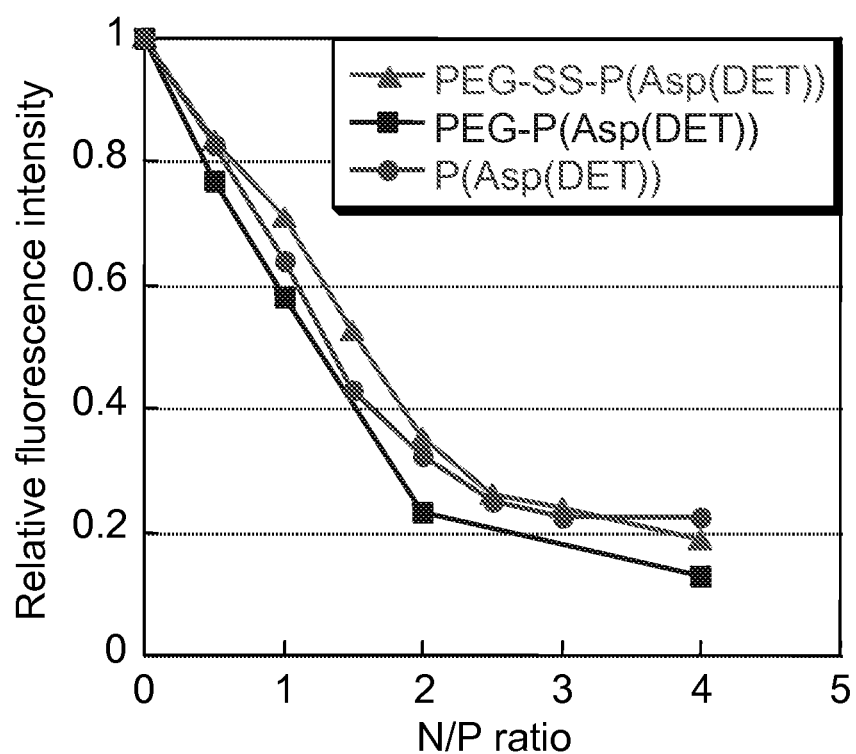
FIG. 8 is a graph showing the results of the ethidium bromide assay of each PIC.

In addition, ethidium bromide (EtBr) was added to the solution obtained in (3) above, and fluorescence was then measured. The results are shown in FIG. 8. For comparison, a block copolymer without an S—S bond (PEG-P(Asp(DET))) or a polymer without PEG (a homopolymer; P(Asp(DET))) (please see the following general formulae) was used instead of PEG-SS-P(Asp(DET)) in (3) above, so as to obtain a solution. The results of ethidium bromide assay performed on the thus obtained solution are also shown in FIG. 8. Since a decrease in fluorescence reached almost a constant value around N/P=2, it is considered that formation of PIC was completed around such N/P value. It is considered that only a primary amine portion of DET is protonated under conditions for PIC formation. Thus, it can be said that N/P=2 is a point at which the polycation charge of the block copolymer and the anion charge of pDNA are just balanced out.

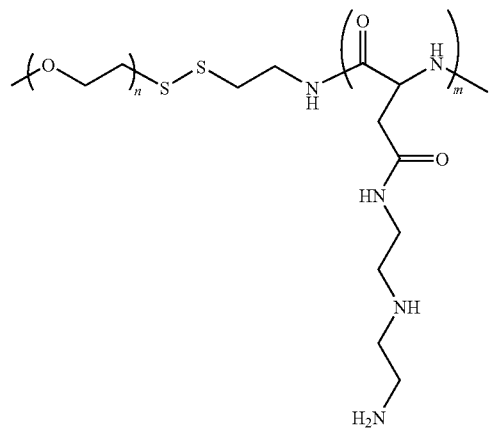

PEG-SS-P(Asp(DET))
with S-S bond
n = 227, m = 100

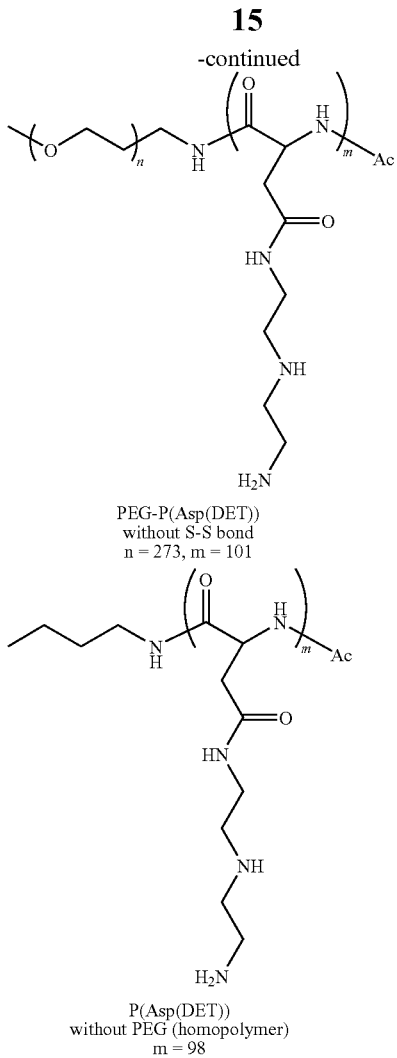

PEG-P(Asp(DET))
without S-S bond
n = 273, m = 101

P(Asp(DET))
without PEG (homopolymer)
m = 98

(5) Measurement of Particle Size

Figure 9:
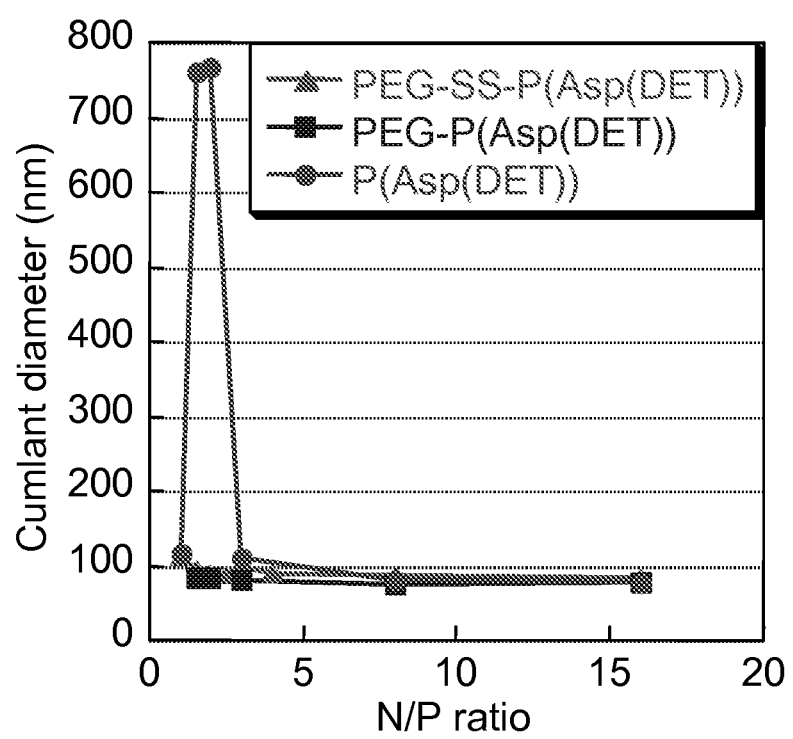
FIG. 9 is a graph showing the measurement results of the particle size of each PIC.

The particle size of PIC was measured by the dynamic light scattering (DLS). The results are shown in FIG. 9. The particle size of PIC comprising PEG-SS-P(Asp(DET)) was approximately 80 nm, regardless of the N/P ratio (PIC comprising PEG-P(Asp(DET)) was also the same as described above). In contrast, the particle size of PIC comprising P(Asp(DET)) was sharply increased around N/P=2. This result demonstrated that PIC agglutinated as a result of neutralization of electric charge. From these result, it can be said that agglutination of PIC comprising PEG-SS-P(Asp(DET)) was suppressed by the steric repulsion effect of PEG that was located at the outermost shell.

(6) Measurement of Zeta Potential

Figure 10:
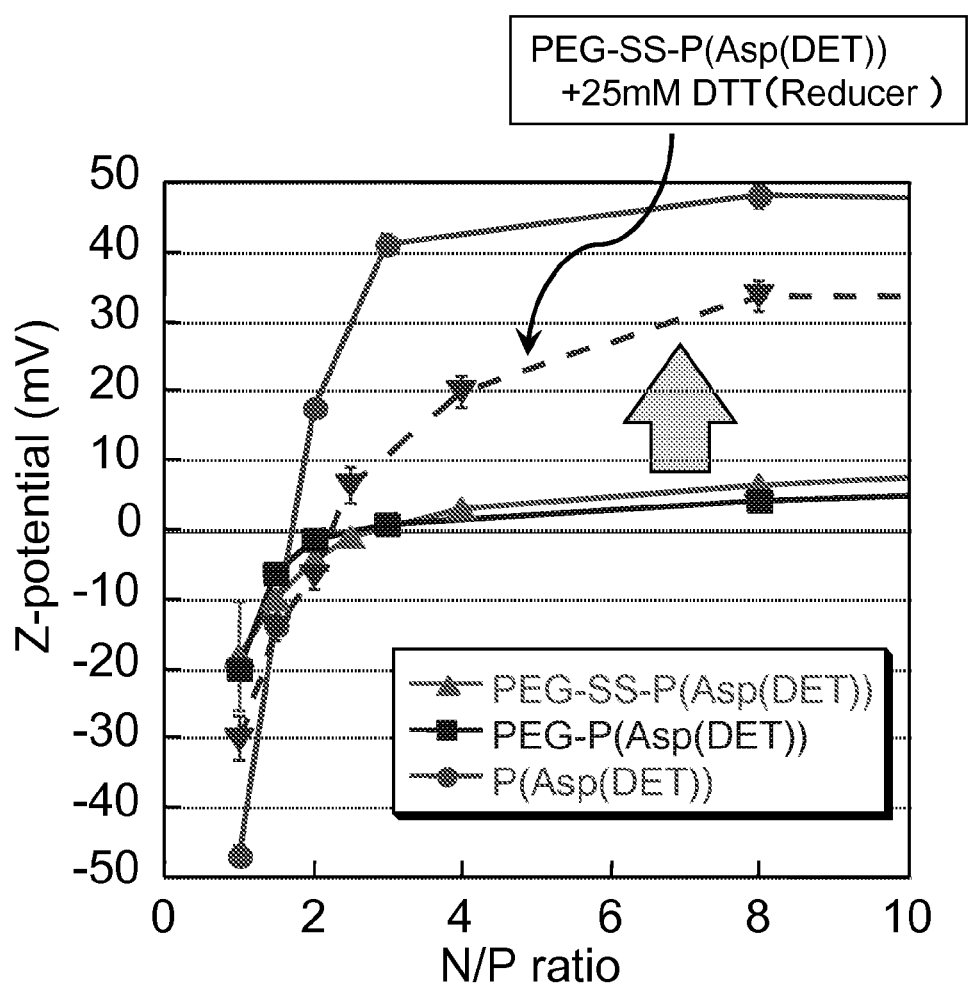
FIG. 10 is a graph showing the measurement results of the zeta potential of each PIC.

The zeta potential of PIC was measured. In the case of PIC comprising PEG-SS-P(Asp(DET)), 25 mM dithiothreitol (DTT) used as a reducer was added to the PIC after measurement, and the zeta potential thereof was measured again. The results are shown in FIG. 10. When compared with PIC comprising P(Asp(DET)) (without PEG), PIC comprising PEG-SS-P(Asp(DET)) or PEG-P(Asp(DET) (with PEG) exhibited a zeta potential close to 0 (zero) even at a high N/P ratio. This result demonstrated that the PEG has a charge-shielding effect. However, after the aforementioned DTT had been added to PIC comprising PEG-SS-P(Asp(DET)), the zeta potential thereof got close to the zeta potential of PIC comprising P(Asp(DET)). This result demonstrated that the S—S bond of PEG-SS-P(Asp(DET)) is cleaved and PEG is separated under a reducing environment. From these results, it can be said that PIC comprising PEG-SS-P(Asp(DET)) is an intelligent carrier, wherein PEG is separated in response to the reducing environment (and the incorporated nucleic acid is released).

EXAMPLE 2

Evaluation of Gene Expression Efficiency

HeLa cells (40,000 cells/well) were inoculated on a 24-well plate, followed by incubation for 24 hours. Subsequently, the PIC comprising "PEG-SS-P(Asp(DET))" obtained in Example 1 was added to the resultant cells in an amount of 1 μg of pDNA per well, and the mixture was then incubated for 24 hours, so as to perform transfection of the HeLa cells with the pDNA. Thereafter, the gene expression level of pDNA was evaluated by luciferase assay (N=4, mean±SE). The gene expression level is obtained in the form of Relative Light Unit (RLU)/mg of protein amount. A case where PIC comprising "PEG-P(Asp(DET)" or PIC comprising "P(Asp(DET))" was used instead of the PIC comprising PEG-SS-P(Asp(DET)) was also evaluated in the same above manner.

Figure 11:
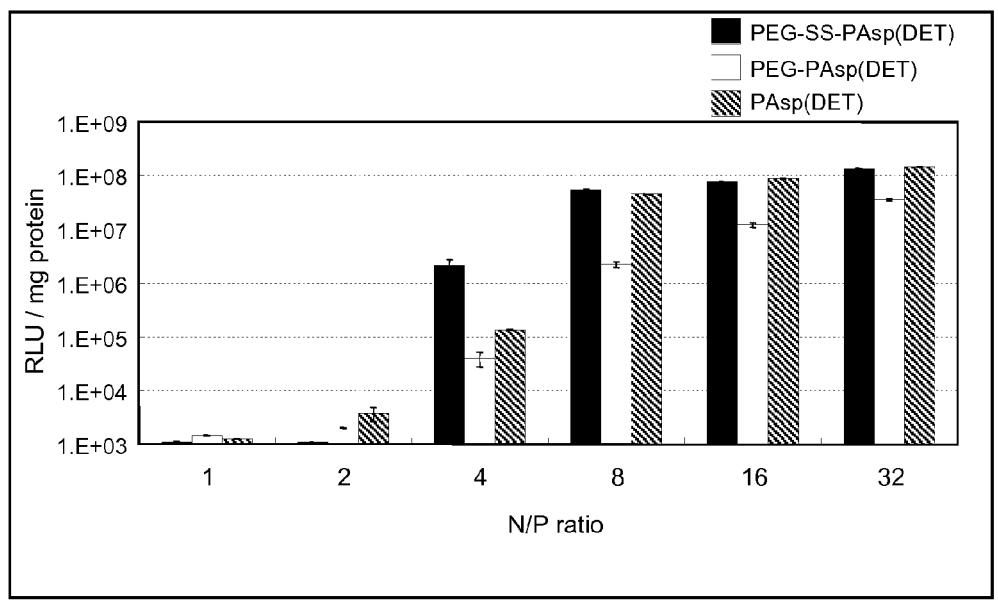
FIG. 11 is a graph showing the evaluation results of gene expression efficiency in transfection using each PIC.

The assay results are shown in FIG. 11. At an N/P ratio of 8 or greater, the gene expression level of the "PIC comprising PEG-SS-P(Asp(DET))" had a higher value than that of the "PIC comprising PEG-P(Asp(DET)" (without an S—S bond) by one or two orders of magnitude, and it exhibited gene expression efficiency at almost the same level as that of the "PIC comprising P(Asp(DET))." Further, at N/P=4, the gene expression efficiency of the "PIC comprising PEG-SS-P(Asp (DET))" exhibited a higher value than that of the "PIC comprising P(Asp(DET)" by an order of magnitude, and thus it exhibited excellent gene expression efficiency. As described above, the "PIC comprising PEG-SS-P(Asp(DET))" exhibited much higher gene expression efficiency than the PIC without an S—S bond, even at a relatively low N/P ratio, by the effect of the S—S bond capable of cleaving under a reducing environment in a cell. Accordingly, it can be said that the PIC comprising PEG-SS-P(Asp(DET)) is an extremely useful environment-responsive gene vector.

INDUSTRIAL APPLICABILITY

The present invention provides a polyion complex exhibiting extremely high gene expression efficiency to a target cell. The polyion complex of the present invention exhibits extremely excellent structural stability when it contains a nucleic acid before being incorporated into a target cell (in blood, etc.). After the polyion complex has been incorporated into a cell (cytoplasm), it becomes extremely useful as an intelligent gene vector, which destroys such structural stability and smoothly releases the nucleic acid contained therein.

Moreover, the present invention also provides a device and a kit for delivering a nucleic acid into a cell, using the aforementioned polyion complex.

The invention claimed is:
1. A polyion complex, which comprises a block copolymer formed by binding polyethylene glycol to a polycation via a disulfide group, and a nucleic acid, wherein the block copolymer is represented by the following general formula (1):

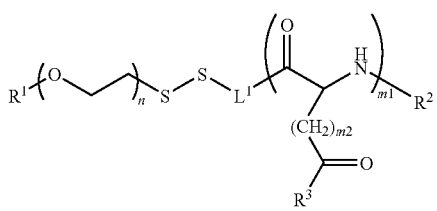

(1)

wherein each of $R^1$ and $R^2$ independently represents a a methyl group; $R^3$ represents —NH—$(CH_2)_2$—NH—$(CH_2)_2$—NH$_2$; $L^1$ represents —$(CH_2)_2$—NH—

—$(CH_2)_{p1}$—NH—  (4);

m1 represents an integer between 30 and 150; m2 represents an integer of 1; and n represents an integer between 100 and 400.

2. The polyion complex according to claim 1, wherein m1 represents an integer of 100; and n represents an integer of 227.

3. The polyion complex according to claim 1, wherein the polycation portion in the block copolymer and the nucleic acid bind to each other by electrostatic interaction.

4. The polyion complex according to claim 1, wherein the nucleic acid and the polycation portion in the block copolymer form a core portion, and a portion containing polyethylene glycol in the block copolymer forms a shell portion around the core portion.

5. A device for delivering a nucleic acid into a cell, which comprises the polyion complex according to claim 1.

6. A method for delivering a nucleic acid into a target cell, which comprises:

administering a solution that contains the polyion complex according to any one of claims 1 to 4 to a test animal so that the polyion complex can be introduced into the target cell;
transferring the polyion complex from the endosome to the cytoplasm;
dissociating the polyion complex in the cell; and
releasing the nucleic acid into the cytoplasm.

7. A block copolymer formed by binding polyethylene glycol to polycation via a disulfide group, wherein the block copolymer is represented by the following general formula (1):

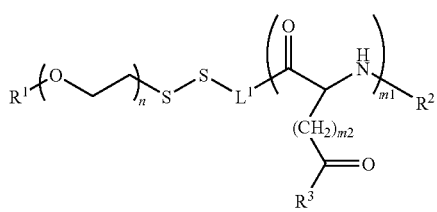

(1)

wherein each of $R^1$ and $R^2$ independently represents a methyl group; $R^3$ represents —NH—$(CH_2)_2$—NH—$(CH_2)_2$—NH$_2$; $L^1$ represents —$(CH_2)_2$—NH—; m1 represents an integer between 30 and 150; m2 represents an integer of 1; and n represents an integer between 100 and 400.

8. The block copolymer according to claim 7, wherein m1 represents an integer of 100; and n represents an integer of 227.

* * * * *